United States Patent [19]
Lang et al.

[11] Patent Number: 5,503,826
[45] Date of Patent: Apr. 2, 1996

[54] HAIR KERATIN-REDUCING MONO, DI- AND TRIGLYCERIDES OF CYSTEINE AND COMPOSITIONS

[75] Inventors: Guenther Lang, Reinheim, Germany; Hans-Juergen Braun, Ueberstorf, Switzerland; Gerhard Maresch, Darmstadt, Germany

[73] Assignee: Wella Aktiengesellschaft, Darmstadt, Germany

[21] Appl. No.: 330,363

[22] Filed: Oct. 27, 1994

[30] Foreign Application Priority Data

Oct. 28, 1993 [DE] Germany ............. 43 36 838.7

[51] Int. Cl.⁶ ..................... A61K 7/09; A61K 7/06
[52] U.S. Cl. ..................... 424/70.51; 424/70.5
[58] Field of Search ............... 424/70.51, 70.5, 424/70.1, 401; 514/665; 132/203

[56] References Cited

U.S. PATENT DOCUMENTS

| | | | |
|---|---|---|---|
| 3,629,452 | 12/1971 | Kalopissis | 514/665 |
| 4,218,435 | 8/1980 | Shiba | 424/70.51 |
| 4,322,401 | 3/1982 | Harada | 424/70.51 |
| 4,956,175 | 9/1990 | Maignan | 424/70.5 |
| 4,992,267 | 12/1991 | DenBeste et al. | 424/71 |
| 5,085,860 | 2/1992 | Junino | 424/70.5 |
| 5,334,377 | 8/1994 | Junino | 424/70.51 |
| 5,350,572 | 9/1994 | Savaides | 424/70.51 |

FOREIGN PATENT DOCUMENTS

| | | | |
|---|---|---|---|
| 0518137 | 12/1992 | European Pat. Off. | |
| 2658424 | 2/1978 | Germany | |
| 192990 | 4/1986 | Japan | 424/70.51 |

*Primary Examiner*—Thurman K. Page
*Assistant Examiner*—Sally Gardner
*Attorney, Agent, or Firm*—Michael J. Striker

[57] ABSTRACT

The new keratin-reducing substances useful in compositions for permanent shaping of hair are glyceryl esters of cysteine, especially the monoglyceryl esters. As monoglyceryl esters of cysteine 2-amino-3-mercaptopropionic acid-(2',3'-dihydroxypropyl)ester and 2-amino-3-mercaptopropionic acid-(1',3'-dihydroxyisopropyl)ester are particularly preferred. A preferred embodiment of the compositions for permanent shaping of hair consists of a ready-to-use mixture of a water-free component including at least one glyceryl ester of cysteine and at least one other component which is kept physically separately from the water-free component until the mixture is prepared. The compositions also can include other conventional ingredients normally used in permanent shaping compositions such as surfactants and thickeners. The compositions have a preferred pH range of 6.0 to 8.5 and contain from 8 to 28 percent by weight of the glyceryl esters of cysteine.

12 Claims, No Drawings

HAIR KERATIN-REDUCING MONO, DI- AND TRIGLYCERIDES OF CYSTEINE AND COMPOSITIONS

BACKGROUND OF THE INVENTION

The present invention relates to compositions for permanent shaping of hair and new hair keratin-reducing cysteine-glycerol esters, i.e. mono-, di- and triglyceryl esters of cysteine, used in those compositions as the effective hair keratin-reducing agent.

Weakly acidic to neutral compositions for permanent shaping of hair are advantageously used for careful permanent shaping of damaged, especially white or dyed, hair. During the past 30 years thioglycolic acid esters have proven to be the best reducing agents for this purpose.

There are however a number of disadvantages opposing the advantages provided by a permanent shaping treatment of hair performed with a weakly acidic to neutral permanent shaping agent. Permanent shaping compositions based on thioglycolate have reduced waveability in comparison to mild alkali shaping agents. For this reason the heat, a lengthening of the treatment time to 20 to 60 minutes and the use of comparatively thin curlers are required. Use of this permanent shaping agent for normal, undamaged natural hair is not accepted or meaningful, because of the required longer treatment time of over 30 minutes and required heat, so the use of weakly acidic to neutral permanent shaping compositions has up to now usually been limited to pre-damaged, easily worked hair.

An additional considerable disadvantage of acidic permanent shaping compositions is the poor eye and skin compatibility and the sensitizing action of thioglycolic acid esters.

Inspite of a number of attempts the present sensitizing effect of acidic permanent shaping compositions could not be decisively reduced.

A mildly alkaline (pH=7.1 to 9) permanent shaping composition, which contains cysteine or its salts as active keratin-reducing agents, has been suggested as an alternative. This hair shaping agent however has a similar series of disadvantages. Cysteine provides only a weak hair shaping effect and has a reduced stability. When cysteine-containing permanent shaping agents are applied to the hair, the cysteine is oxidized quickly by the oxygen in the air to the weakly soluble cystine in water, which forms a difficult-to-remove white coating which is deposited on the hair.

SUMMARY OF THE INVENTION

It is an object of the present invention to provide a composition for the permanent shaping of hair which provides a careful and uniform shaping of the hair both in acidic and also weakly alkaline conditions (pH=4.5 to 9.0), but has no or only a slight tendency to cause allergies and forms no troublesome deposit or coating on the hair.

Surprisingly it has been found that a composition for permanent shaping of hair containing glyceryl esters of cysteine provides a uniform hair shaping and can be used with damaged as well as undamaged hair without causing the frequently observed allergic skin reactions that have been observed to occur with keratin-reducing ester compounds currently used in hair shaping compositions and without forming the troublesome coating observed with cysteine-containing permanent shaping compositions.

According to the present invention, a particularly advantageous composition for the permanent shaping of hair based on an effective keratin-reducing substance includes the glyceryl esters of cysteine, or cysteine-glycerol esters, as the effective keratin-reducing substance.

The "glyceryl esters of cysteine" here include the mono-, di- and/or triglyceryl of cysteine. Of these glyceryl esters the monoglyceryl esters of cysteine are particularly preferred. In the following disclosure the mono-, di- and/or triglyceryl esters of cysteine are referred to as "cysteine-glycerol esters".

Of course it is also possible to use the cysteine-glycerol esters together with other hair keratin-reducing agents—such as for example thioglycolic acid, thiolactic acid, 3-hydroxy-2-mercaptopropionic acid, cysteamine and cysteamine derivatives or cysteine and cysteine derivatives, however the use of cysteine-glycerol esters alone as the sole keratin-reducing substance (that means without additional keratin-reducing substances or compounds) is particularly preferred and essential to avoid the any disadvantages accompanying the other conventional keratin-reducing agent.

The cysteine-glycerol ester is used in the ready composition for the permanent shaping of hair according to the invention in an amount of from 4 to 30 percent by weight, advantageously from 8 to 28 percent by weight.

The ready permanent hair shaping composition according to the invention has a pH of from 4.5 to 9.0, advantageously 6.0 to 8.5.

The permanent hair shaping composition can be in the form of an aqueous solution or an emulsion and also in thickened form on an aqueous basis, especially as a gel, cream or paste.

Understandably the permanent shaping composition according to the invention can contain any of the known additive ingredients used in these type of compositions, for example, thickeners, such as kaolin, bentonite, fatty acids, higher fatty alcohols, starches, polyacrylic acids and their derivatives, cellulose derivatives, alginate, Vaseline or paraffin oil; wetting agents or emulsifiers selected from the classes of anionic, cationic, amphoteric or nonionic surface active substances, such as fatty alcohol sulfates, fatty alcohol ether sulfates, alkyl sulfonates, alkyl benzene sulfates, quaternary ammonium salts, alkyl betaines, ethoxylated alkylphenols, fatty acid alkanol amides or ethoxylated fatty acid esters; additional turbidity causing agents, for example polyethylene glycol esters; or alcohols, such as ethanol, propanol, isopropanol or glycerol; solvating agents; stabilizers; buffer substances; perfume oils; dyes and hair conditioning and hair care ingredients, such as cationic polymers, lanolin derivatives, cholesterol, pantothenic acid or betaine. The above-mentioned additive ingredients can be contained in the composition according to the invention in amounts which are standard for that purpose, for example the wetting and emulsifying agents, in a concentration of 0.2 to 30 percent by weight, while the thickening agents, in an amount of 0.5 to 20 percent by weight.

The so-called swelling and penetrating agents, for example dipropyleneglycolmonomethyl ether, 2-pyrrolidone or imidazolidin-2-one, which are often added to improve the effectiveness of compositions of this type, can be added to the composition according to the invention in amounts of 2 to 30 percent by weight. Dithiocompounds, for example dithiodiglycolic acid, dithiodilactic acid or their salts, can also be added.

Since carboxylic acid esters in aqueous media are stable only for a limited time and, particularly in the alkaline region, since they can be easily hydrolyzed, the cysteine-glycerol esters are advantageously separately packaged in water-free form and the composition for permanent shaping of hair is made directly prior to use by mixing of the components containing the cysteine-glycerol esters with one or more additional components.

According to the packaging the composition according to the invention can be provided in the form of a two- or three component preparation.

Thus the composition for permanent shaping of hair according to the invention can be made for example by mixing of two components, of which the first component contains the alkalizing agent, for example an alkali metal carbonate, ammonium carbonate, alkali metal hydrogen carbonate or ammonium hydrogen carbonate, as well as the above-described cosmetic additive ingredients and water, while the second water-free component contains the cysteine-glycerol esters.

Similarly it is also possible to package the composition according to the invention in the form of a three-component preparation in which one component contains a portion of the above-described cosmetic additive ingredients, a second component contains the cysteine-glycerol esters and is water-free, and the third component contains perfume oil, solvating agents and hair care materials in aqueous solution or in water-free form.

In all embodiments of the composition according to the invention the above-described cosmetic additives can be contained in the aqueous component and/or in the nonaqueous component or components.

The composition for permanent shaping of hair according to the invention made in the above-described manner is made suitable for any hair type or structure by the variation of pH, if necessary with addition of heat. This composition can be used to provide an elastic, permanent uniform shaping of the hair from the hair roots to hair tips.

The permanent shaping of hair using the composition according to the invention is performed according to the standard method, which includes treating the hair with the composition according to the invention before and/or after bringing it into the desired shape, rinsing the hair with water, performing an oxidative after-treatment, rinsing with water, subjecting the hair to a water jet if necessary and then drying the hair.

The hair can be washed with a shampoo prior to treatment and after that rinsed with water. Subsequently the hand-towel dried hair is divided into individual strands and wound on curlers with a diameter of from 5 to 30 millimeters, advantageously 5 to 15 millimeters. Then the hair is treated with an effective amount, advantageously from 60 to 120 grams, of the above-described composition according to the invention for permanent shaping of hair.

After a sufficient treatment time for effective permanent shaping of the hair, which, according to the hair condition, the pH value and the shaping effectiveness of the composition and according to the temperature, amounts to from 5 to 30 minutes (10 to 30 minutes without heating but 5 to 20 minutes with heating), the hair is rinsed with water and then oxidatively after-treated ("fixed"). The after-treatment is, according to the hair feel, advantageously used in an amount of 80 to 100 grams.

Any currently known oxidative after-treatment composition can be used for the oxidative after-treatment step according to the invention. Potassium and sodium bromate, sodium perborate, urea peroxide and hydrogen peroxide can, for example, be used in this type of oxidative-aftertreatment composition. The concentration of the oxidizing agent differs depending on the application time (usually 5 to 15 minutes) and the application temperature. Usually the oxidizing agent is present in the ready aqueous after-treatment composition in a concentration of 0.5 to 10 percent by weight. The composition for oxidative after-treatment can contain additional materials, such as wetting agents, hair care materials such as cationic polymers, weak acids, buffer substances or peroxide stabilizers and can be present in the form of an aqueous solution, an emulsion and in thickened form on an aqueous basis, for example as a cream, gel or paste.

Subsequently the curlers are removed. As required, the curled hair can be now after-treated with the oxidative after-treatment composition. Then the hair is rinsed with water, treated with a water jet as necessary and subsequently dried.

The cysteine-glycerol ester contained in the composition according to the invention for shaping hair can be obtained in the standard way by esterification of cysteine in the presence of acid catalysts, e.g. sulfuric acid, hydrochloric acid or benzene sulfonic acid, with glycerol, advantageously with heating.

It is also however possible to prepare cysteine monoglyceryl ester by alkylation of the disodium salt of cystine with 3-chloro- or 3-bromo-1,2-propandiol and subsequently reducing the cystine-diglyceryl esters obtained therefrom.

The above-described cysteine-glyceryl esters provide a high waveability in acidic to mildly alkaline compositions, have nearly a neutral odor and are water soluble. They have outstanding physiological compatibility and good stability in water.

The cysteine-glycerol esters are not known in the Chemical literature.

Thus the subject matter of the present invention also includes cysteine-glycerol esters, the mono-, di- and triglyceryl esters of cysteine.

The monoglyceryl esters of cysteine, 2-amino-3-mercaptopropionic acid-(2',3'-dihydroxypropyl) ester of formula I and 2-amino-3-mercaptopropionic acid-(1',3'-dihydroxyisopropyl) ester of formula II alone or in combination with each other, are particularly preferred.

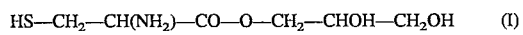

$$HS—CH_2—CH(NH_2)—CO—O—CH_2—CHOH—CH_2OH \qquad (I)$$

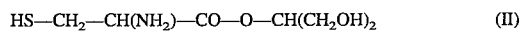

$$HS—CH_2—CH(NH_2)—CO—O—CH(CH_2OH)_2 \qquad (II)$$

The following examples illustrate the subject matter of the invention.

EXAMPLES

Example 1

Two-component Hair Shaping Composition

| | |
|---|---|
| Component 1: | 3.0 g Urea |
| | 1.0 g Octylphenol, ethoxylated with 20 Mol of ethylene oxide |
| | 0.8 g ammonia (25 percent aqueous solution) |
| | 0.5 g perfume oil |
| | 0.3 g ammonium hydrogen carbonate |
| | 94.4 g water, desalinized |
| | 100.0 |
| Component 2: | 70.0 g monoglyceryl ester of cysteine of Example 4 |

|   |   |
|---|---|
| | 30.0 g glycerol |
| | 100.0 |

70 grams of component 1 and 30 grams of component 2 were mixed to form a hair shaping composition with a pH value of 6.3 prior to use.

Mildly damaged hair is washed with a shampoo and rinsed with water. Subsequently the rubbed hair is wound on curlers with a diameter of 8 millimeters, uniformly moistened with the hair shaping composition and covered with a plastic bonnet. After an acting time of 15 minutes at 400° C. the plastic bonnet is removed, the hair is rinsed with water and the hair is subjected to an oxidative after-treatment with 100 grams of a 3 percent hydrogen peroxide solution.

After removing the curlers the hair is again rinsed and after that dried.

This treatment provides a uniform natural effective shaping of the hair from the hair roots to hair tips.

Example 2

Two component Hair Shaping Composition

| Component 1: | 2.0 g Dipropyleneglycolmonomethyl ether |
| --- | --- |
| | 0.3 g Coconut oil fatty acid, ethoxylated with 10 Mol of ethylene oxide |
| | 1.0 g ammonia (25 percent aqueous solution) |
| | 0.3 g perfume oil |
| | 0.2 g diammoniumdithiodiglycolate |
| | 96.2 g water, desalinized |
| | 100.0 |
| Component 2: | 60.0 g monoglyceryl ester of cysteine of Example 4 |
| | 10.0 N-acetylcysteamine |
| | 30.0 g glycerol |
| | 100.0 |

80 grams of component 1 are mixed with 40 grams of component 2 to form a ready hair shaping composition according to the invention with a pH of 6.5.

Normal undamaged hair is washed, rubbed with a hand towel and wound on curlers with a diameter of 6 millimeters. Subsequently the hair is uniformly moistened with the above-described hair shaping composition. After an acting time of 20 minutes the hair is rinsed with water and then after-treated with 80 grams of a 3 percent aqueous hydrogen peroxide solution. After removing the curlers the hair is rinsed again with water, subjected to a water jet and subsequently dried.

The hair thus treated has a uniform curl over its entire hair length, which is comparable with the curl obtained by treatment with a mild alkaline hair treatment agent.

Example 3

Three component—Hair Shaping Composition

| Component 1: | 1.9 g 1,2-propyleneglycol |
| --- | --- |
| | 1.0 g glyceryl diacetate |
| | 0.8 g coconut oil fatty alcohol, ethoxylated with 10 Mol of ethylene oxide |
| | 0.3 g perfume oil |
| Component 2: | 4.0 g Urea |
| | 1.5 g ammonia (25 percent aqueous solution) |
| | 1.2 g ammonium hydrogen carbonate |
| | 89.3 g water |
| Component 1 + 2 | 100.0 |
| Component 3: | 80.0 g monoglyceryl ester of cysteine of Example 4 |
| | 20.0 g glycerol |
| | 100.0 |

Component 1 is dissolved in component 2 immediately prior to use. Subsequently 70 grams of this solution are mixed with 30 grams of component 3. The pH value of the ready permanent shaping composition amounts to 6.8.

Hair of nonuniform hair quality is washed, rubbed with a hand towel and wound on curlers with a diameter of 6 millimeters. Subsequently the hair is uniformly moistened with the above-described ready hair shaping composition.

After an acting time of 15 minutes at 40° C. the hair is rinsed with water, subjected to a water jet and subsequently dried.

A more uniformly shaped hair with better springiness and flexibility results from this treatment.

Production Example

Example 4

2-amino-3-mercaptopropionic acid-(2',3'-dihydroxypropyl) ester

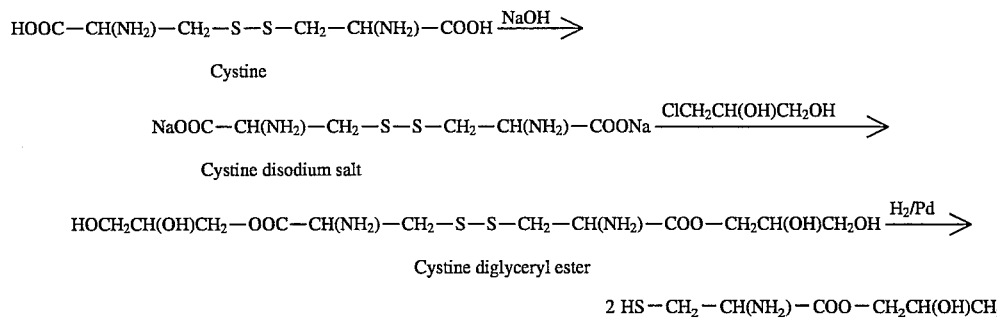

25.6 g (0.09 Mol) of dry Cystine disodium salt, made from cystine and sodium hydroxide in the required amount, are heated together with 31 g (0.20 mol) 3-bromo-1,2-propanediol in 50 ml glycoldimethyl ether for 3 hours under reflux conditions. The solvent is subsequently distilled away, the residue received in dilute hydrochloric acid and then hydrogenated in the presence of a palladium/activated carbon catalyst. After receiving the calculated amount of hydrogen, the catalyst is filtered, the filtrate is neutralized and subsequently extracted with methylene chloride. After drying the methylene chloride phase over magnesium sulfate and distilling the methylene chloride solvent away one obtains a 14 g yield ($\simeq$39.8% of the theoretical yield) of an oily product ($\simeq$2-amino-3-mercaptopropionic acid-( 2',3'-dihydroxypropyl)ester) which can be used in the composition for permanently shaping hair without additional purification.

Example 5

2-amino-3-mercaptopropionic acid-(2',3'-dihydroxypropyl)ester $$HS-CH_2-CH(NH_2)-COOH +$$

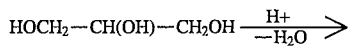

$$HS-CH_2-CH(NH_2)-COOCH_2-CH(OH)-CH_2OH$$

12.1 g (0.1 Mol) L-cysteine are heated together with 100 ml glycerol and 50 ml 3N hydrochloric acid for 3 hours at 90° C.

Subsequently the water produced by the reaction is distilled away at 30 mbar (distillation time: 3 hours).

The distillation residue contained according to thin layer chromatography (stationary phase: silica gel 60; eluting agent: methanol/water/pyridine 80/20/4; $r_f$-value (cysteine monoglyceryl ester)=0.75) no cysteine. The 2-amino-3-mercaptopropionic acid-( 2',3'-dihydroxypropyl)ester) can be used in the composition for permanently shaping hair without further purification. Product Mass Spectrum: (70 ev): m/e=196 ($M^+$), 122, 93, 75, 57.

All percentages in the above specification are percentages by weight unless otherwise indicated.

While the invention has been illustrated and described as embodied in hair keratin-reducing mono-, di- and triglycerides of cysteine and compositions for permanent shaping of hair containing them, it is not intended to be limited to the details shown, since various modifications and structural changes may be made without departing from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

What is claimed is:.

1. Composition for permanent shaping of hair, having a pH of 4.5 to 9.0 and containing from 4 to 30 percent by weight of at least one glyceryl ester of cysteine as a hair keratin-reducing substance effective in the permanent shaping of hair.

2. Composition as defined in claim 1, wherein said at least one glyceryl ester of cysteine is a monoglyceryl ester of cysteine.

3. Composition as defined in claim 1, wherein said at least one glyceryl ester of cysteine is present in an amount of from 8 to 28 percent by weight.

4. Composition as defined in claim 1, wherein said pH is from 6.0 to 8.5.

5. Composition as defined in claim 1, consisting of a ready-to-use mixture of a water-free component including said at least one glyceryl ester of cysteine, and at least one other component consisting essentially of at least one alkalizing agent, at least one cosmetic ingredient and water, said at least one other component being separate from said water-free component until said ready-to-use mixture is formed by mixing said components.

6. Composition as defined in claim 1, further comprising at least one cosmetic ingredient selected from the group consisting of thickeners; anionic, cationic, amphoteric or nonionic surface active substances; turbidity-causing agents; solvating agents; stabilizers; buffer substances; perfume oils; hair dyes and hair conditioning ingredients.

7. Composition as defined in claim 1, wherein said hair keratin-reducing substance comprises said at least one glyceryl ester of cysteine and containing no other hair keratin-reducing substances.

8. Composition for permanent shaping of hair having a pH of from 4.5 to 9.0 and containing from 4 to 30 percent by weight of at least one glyceryl ester of cysteine as a hair keratin-reducing substance effective in the permanent shaping of the hair; water; and at least one cosmetic ingredient selected from the group consisting of thickeners; anionic, cationic, amphoteric or nonionic surface active substances; turbidity-causing agents; solvating agents; stabilizers; buffer substances; perfume oils; hair dyes and hair conditioning ingredients; wherein said hair keratin-reducing substance comprises said at least one glyceryl ester of cysteine and containing no other hair keratin-reducing substances.

9. Composition as defined in claim 8, wherein said at least one glyceryl ester of cysteine is a monoglyceryl ester of cysteine.

10. Composition as defined in claim 8, wherein said at least one glyceryl ester of cysteine is present in an amount of from 8 to 28 percent by weight.

11. Composition as defined in claim 8, wherein said pH is from 6.0 to 8.5.

12. Composition as defined in claim 8 consisting of a ready-to-use mixture of a water-free component including said at least one glyceryl ester of cysteine, and at least one other component consisting essentially of at least one alkalizing agent, at least one cosmetic ingredient and water, said at least one other component being separate from said water-free component until said ready-to-use mixture is formed by mixing said components.

* * * * *